United States Patent
Noguchi et al.

(10) Patent No.: US 11,396,486 B2
(45) Date of Patent: Jul. 26, 2022

(54) COMPOUND CONTAINING UNSATURATED DOUBLE BOND, OXYGEN ABSORBENT USING SAME AND RESIN COMPOSITION

(71) Applicant: KURARAY CO., LTD., Okayama (JP)

(72) Inventors: Daiki Noguchi, Niigata (JP); Takashi Fukumoto, Niigata (JP)

(73) Assignee: KURARAY CO., LTD., Okayama (JP)

( * ) Notice: Subject to any disclaimer, the term of this patent is extended or adjusted under 35 U.S.C. 154(b) by 0 days.

(21) Appl. No.: 17/048,185

(22) PCT Filed: Apr. 11, 2019

(86) PCT No.: PCT/JP2019/015850
§ 371 (c)(1),
(2) Date: Oct. 16, 2020

(87) PCT Pub. No.: WO2019/203131
PCT Pub. Date: Oct. 24, 2019

(65) Prior Publication Data
US 2021/0163391 A1    Jun. 3, 2021

(30) Foreign Application Priority Data
Apr. 19, 2018 (JP) .............................. JP2018-080815

(51) Int. Cl.
| | | |
|---|---|---|
| C07C 43/178 | (2006.01) |
| C07C 43/15 | (2006.01) |
| C08K 5/05 | (2006.01) |
| C08K 5/098 | (2006.01) |
| C07C 69/54 | (2006.01) |
| B01J 20/22 | (2006.01) |
| C08L 101/00 | (2006.01) |

(52) U.S. Cl.
CPC ........... *C07C 43/178* (2013.01); *B01J 20/223* (2013.01); *C07C 43/15* (2013.01); *C07C 43/1785* (2013.01); *C07C 69/54* (2013.01); *C08K 5/05* (2013.01); *C08K 5/098* (2013.01); *C08L 101/00* (2013.01)

(58) Field of Classification Search
CPC ... C07C 43/15; C07C 43/178; C07C 43/1785; C07C 69/54
See application file for complete search history.

(56) References Cited

U.S. PATENT DOCUMENTS 3,644,568 A    2/1972    Tilley et al.

FOREIGN PATENT DOCUMENTS

| CH | 632983 A5 * | 11/1982 | ............ C07C 43/15 |
|---|---|---|---|
| EP | 0365996 A2 | 5/1990 | |
| JP | S61-101518 A | 5/1986 | |
| JP | S63-130610 A | 6/1988 | |
| JP | H05-078459 A | 3/1993 | |
| JP | H09-188645 A | 7/1997 | |
| JP | 2009-215399 A | 9/2009 | |
| WO | WO 2018/088206 A1 | 5/2018 | |
| WO | WO 2019/107252 A1 | 6/2019 | |

OTHER PUBLICATIONS

Co-pending U.S. Appl. No. 17/601,998 (Year: 2021).*
Funakoshi et al. ("Insight into the Cyclization of 6-Octen-1-als with Rhodium(I) Complex", Chem. Pharm. Bull. vol. 37, No. 8, Aug. 1989, pp. 1990-1994. (Year: 1989).*
Li et al. ("Regioselective Reductive Hydration of Alkynes To Form Branched or Linear Alcohols", Journal of the American Chemical Society, Oct. 2012, vol. 134, No. 42, pp. 17376-17379). (Year: 2012).*
ISR for PCT/JP2019/015850, dated Jul. 16, 20.19 (w/translation).
Appending et al., "Homologues and Isomers of Noladin Ether, a Putative Novel Endocannabinoid: Interaction with Rat Cannabinoid CB1 Receptors", Bioorganic and Medicinal Chemistry Letters, vol. 13, 2003, pp. 43-46.
Gordillo et al., "Palladium-Catalysed Telomerisation of Isoprene with Glycerol and Polyethylene Glycol: A Facile Route to New Terpene Derivatives", Advanced Synthesis and Catalysis, vol. 351, 2009, pp. 325-330.
EESR for EP App No. 19788967.8, dated Feb. 18, 2022.

* cited by examiner

*Primary Examiner* — Rosalynd A Keys
(74) *Attorney, Agent, or Firm* — Greenblum & Bernstein, P.L.C.

(57) ABSTRACT

An unsaturated double bond-containing compound represented by the general formula (I) or the general formula (II), an oxygen absorbent containing the compound, and a resin composition.

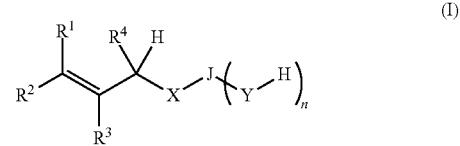

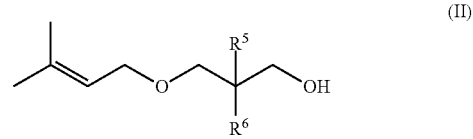

7 Claims, No Drawings

COMPOUND CONTAINING UNSATURATED DOUBLE BOND, OXYGEN ABSORBENT USING SAME AND RESIN COMPOSITION

TECHNICAL FIELD

The present invention relates to a specific unsaturated double bond-containing compound, an oxygen absorbent containing the compound, and a resin composition.

BACKGROUND ART

A radical-polymerizable resin such as an unsaturated polyester resin usable for coating materials and the like has an unsaturated bond in the polymer main chain and is crosslinked to cure with a vinylic crosslinking agent. When such a radical-polymerizable resin is used in coating materials, in general, it is crosslinked in an air atmosphere and is therefore often retarded by oxygen in air, causing a problem of delayed curing and a problem of surface stickiness. As a means for solving the problems, $PTL_s$ 1 and 2 propose a technique of adding an oxygen absorbent to the resin. In addition, as the oxygen absorbent, $PTL_s$ 3 and 4 describe an allyl glycidyl ether.

CITATION LIST

Patent Literature

PTL 1: JP 63-130610 A
PTL 2: JP 5-78459 A
PTL 3: JP 61-101518 A
PTL 4: U.S. Pat. No. 3,644,568

SUMMARY OF INVENTION

Technical Problem

In use for coating materials, heretofore, styrene or the like has been much used as a reactive diluent, but from the viewpoint of environmental protection, there occurs an increasing tendency toward use of hardly-volatile (meth) acrylates. However, use of (meth)acrylates more often faces a problem of inactivation by oxygen than use of hitherto-existing reactive diluents.

The present invention has been made in consideration of the above-mentioned hitherto-existing problems, and an object thereof is to provide an unsaturated double bond-containing compound having an oxygen absorption performance which, when used in coating materials and the like, can sufficiently achieve crosslinking reaction and curing reaction. Another object of the invention is to provide an oxygen absorbent containing the unsaturated double bond-containing compound, and a resin composition containing the oxygen absorbent.

Solution to Problem

The present inventors have made assiduous studies and, as a result, have found that an unsaturated double bond-containing compound represented by the following general formula (I) can stabilize generated radicals more than already-existing oxygen absorbents, and can exhibit a higher oxygen radical scavenging activity, that is, oxygen absorption performance. Based on this finding, the present inventors have made further studies and have completed the present invention.

Specifically, the present invention provides the following [1] to [11].

[1] An unsaturated double bond-containing compound represented by the following formula (I):

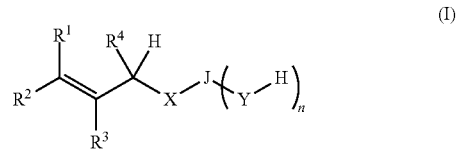

wherein X and Y each independently represent a chalcogen atom, $R^1$ and $R^2$ each independently represent any of an alkyl group having 1 to 6 carbon atoms, an alkenyl group having 2 to 6 carbon atoms, an aryl group, and an aralkyl group, $R^3$ and $R^4$ each independently represent any of a hydrogen atom, an alkyl group having 1 to 6 carbon atoms, an alkenyl group having 2 to 6 carbon atoms, an aryl group, and an aralkyl group, J represents a linking group of an aliphatic hydrocarbon having 3 to 15 carbon atoms, and in the linking group, any arbitrary carbon atom may be replaced by an oxygen atom, and the linking group may have at least one substituent selected from the group consisting of a (meth)acryloyloxy group, a styryloxy group, and an alkenyloxy group having 2 to 5 carbon atoms, n represents an integer of 1 to 5, and when the compound has plural Y's, they may be different atoms.

[2] The unsaturated double bond-containing compound according to [1], wherein X and Y in the general formula (I) each are an oxygen atom.

[3] The unsaturated double bond-containing compound according to [1] or [2], wherein $R^3$ in the general formula (I) is a hydrogen atom.

[4] The unsaturated double bond-containing compound according to any of [1] to [3], wherein $R^4$ in the general formula (I) is a hydrogen atom or a methyl group.

[5] The unsaturated double bond-containing compound according to any of [1] to [4], represented by the following general formula (II):

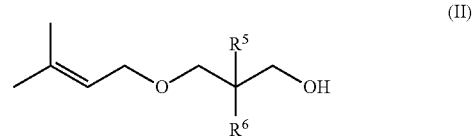

wherein $R^5$ represents a hydrogen atom or a methyl group, $R^6$ represents any of a hydroxy group, a (meth)acryloyloxy group, a styryloxy group, and an alkenyloxy group having 2 to 5 carbon atoms.

[6] The unsaturated double bond-containing compound according to [5], wherein $R^5$ in the general formula (II) is a hydrogen atom.

[7] The unsaturated double bond-containing compound according to [5] or [6], wherein $R^6$ in the general formula (II) is a hydroxy group.

[8] An oxygen absorbent containing the unsaturated double bond-containing compound of any of [1] to [7].

[9] The oxygen absorbent according to [8], containing a transition metal salt in an amount of 0.001 to 10 mol % relative to the vinyl group in the unsaturated double bond-containing compound.

[10] A resin composition containing the oxygen absorbent of [8] or [9], and a resin.

[11] The resin composition according to [10], wherein the resin is an active energy ray-curable resin.

Advantageous Effects of Invention

According to the present invention, there can be provided an unsaturated double bond-containing compound having an oxygen absorption performance which, when used in coating materials and the like, can sufficiently achieve cross-linking reaction and curing reaction. There can be also provided an oxygen absorbent containing the unsaturated double bond-containing compound, and a resin composition containing the oxygen absorbent.

DESCRIPTION OF EMBODIMENTS

[Unsaturated Double Bond-Containing Compound]

The unsaturated double bond-containing compound of the present invention is a compound represented by the following formula (I):

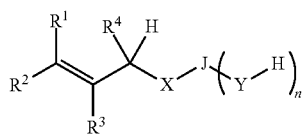

wherein X and Y each independently represent a chalcogen atom, $R^1$ and $R^2$ each independently represent any of an alkyl group having 1 to 6 carbon atoms, an alkenyl group having 2 to 6 carbon atoms, an aryl group, and an aralkyl group, $R^3$ and $R^4$ each independently represent any of a hydrogen atom, an alkyl group having 1 to 6 carbon atoms, an alkenyl group having 2 to 6 carbon atoms, an aryl group, and an aralkyl group, J represents a linking group of an aliphatic hydrocarbon having 3 to 15 carbon atoms, and in the linking group, any arbitrary carbon atom may be replaced by an oxygen atom, and the linking group may have at least one substituent selected from the group consisting of a (meth)acryloyloxy group, a styryloxy group, and an alkenyloxy group having 2 to 5 carbon atoms, n represents an integer of 1 to 5, and when the compound has plural Y's, they may be different atoms.

In the general formula (I), X and Y each independently represent a chalcogen atom. X and Y each are, from the viewpoint of easiness in production of the unsaturated double bond-containing compound, and from the viewpoint of improving the oxygen absorption performance, preferably an oxygen atom or a sulfur atom, more preferably an oxygen atom.

In the general formula (I), $R^1$ and $R^2$ each independently represent any of an alkyl group having 1 to 6 carbon atoms, an alkenyl group having 2 to 6 carbon atoms, an aryl group, and an aralkyl group.

Examples of the alkyl group having 1 to 6 carbon atoms include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, a cyclopropyl group, a cyclobutyl group, a cyclopentyl group, and a cyclohexyl group.

Examples of the alkenyl group having 2 to 6 carbon atoms include a vinyl group, an allyl group, a 1-propenyl group, a 2-propenyl group, an isopropenyl group, a butenyl group, an isobutenyl group, a pentenyl group, a hexenyl group, a cis-3-hexenyl group, and a cyclohexenyl group.

Examples of the aryl group include a phenyl group, a tolyl group, a xylyl group and a naphthyl group.

Examples of the aralkyl group include a benzyl group, a 2-phenylethyl group, a 2-naphthylethyl group, and a diphenylmethyl group.

Among these, preferably, $R^1$ and $R^2$ each are independently any of an alkyl group having 1 to 6 carbon atoms and an alkenyl group having 2 to 6 carbon atoms, more preferably an alkyl group having 1 to 4 carbon atoms, even more preferably a methyl group.

In the general formula (I), $R^3$ and $R^4$ each independently represent any of a hydrogen atom, an alkyl group having 1 to 6 carbon atoms, an alkenyl group having 2 to 6 carbon atoms, an aryl group, and an aralkyl group.

Examples of the alkyl group having 1 to 6 carbon atoms include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, a cyclopropyl group, a cyclobutyl group, a cyclopentyl group, and a cyclohexyl group.

Examples of the alkenyl group having 2 to 6 carbon atoms include a vinyl group, an allyl group, a 1-propenyl group, a 2-propenyl group, an isopropenyl group, a butenyl group, an isobutenyl group, a pentenyl group, a hexenyl group, a cis-3-hexenyl group, and a cyclohexenyl group.

Examples of the aryl group include a phenyl group, a tolyl group, a xylyl group and a naphthyl group.

Examples of the aralkyl group include a benzyl group, a 2-phenylethyl group, a 2-naphthylethyl group, and a diphenylmethyl group.

Among these, preferably, $R^3$ and $R^4$ each are independently any of a hydrogen atom, an alkyl group having 1 to 3 carbon atoms, an alkenyl group having 2 or 3 carbon atoms and an aryl group, more preferably a hydrogen atom or a methyl group, even more preferably a hydrogen atom. Above all, from the viewpoint of improving the oxygen absorption performance of the unsaturated double bond-containing compound, $R^3$ is preferably a hydrogen atom, $R^4$ is preferably a hydrogen atom or a methyl group, and more preferably, both are hydrogen atoms.

In the general formula (I), J represents a linking group of an aliphatic hydrocarbon having 3 to 15 carbon atoms, and in the linking group, any arbitrary carbon atom may be replaced by an oxygen atom, and the linking group may have at least one substituent selected from the group consisting of a (meth)acryloyloxy group, a styryloxy group, and an alkenyloxy group having 2 to 5 carbon atoms.

The linking group is, from the viewpoint of easiness in handling the unsaturated double bond-containing compound, preferably an aliphatic hydrocarbon group having 3 to 10 carbon atoms, more preferably an aliphatic hydrocarbon group having 3 to 5 carbon atoms.

The linking group may have at least one substituent selected from the group consisting of a (meth)acryloyloxy group, a styryloxy group, and an alkenyloxy group having 2 to 5 carbon atoms. Examples of the styryloxy group include a 4-vinylphenoxy group. The alkenyloxy group having 2 to 5 carbon atoms may also be a vinyloxy group having 2 to 5 carbon atoms.

The substituent that the linking group has is, from the viewpoint of improving the oxygen absorption performance of the unsaturated double bond-containing compound, preferably a (meth)acryloyloxy group.

Specific examples of the linking group include a linking group having any of the structures represented by the following general formula (J-1), and from the viewpoint of easy availability of raw materials, a linking group represented by the following general formula (J-2) is preferred, and from the viewpoint of improving the oxygen absorption performance of the unsaturated double bond-containing compound, a linking group represented by the following general formula (J-3) is more preferred. In the general formulae (J-1) to (J-3), *indicates a bonding point to X or Y.

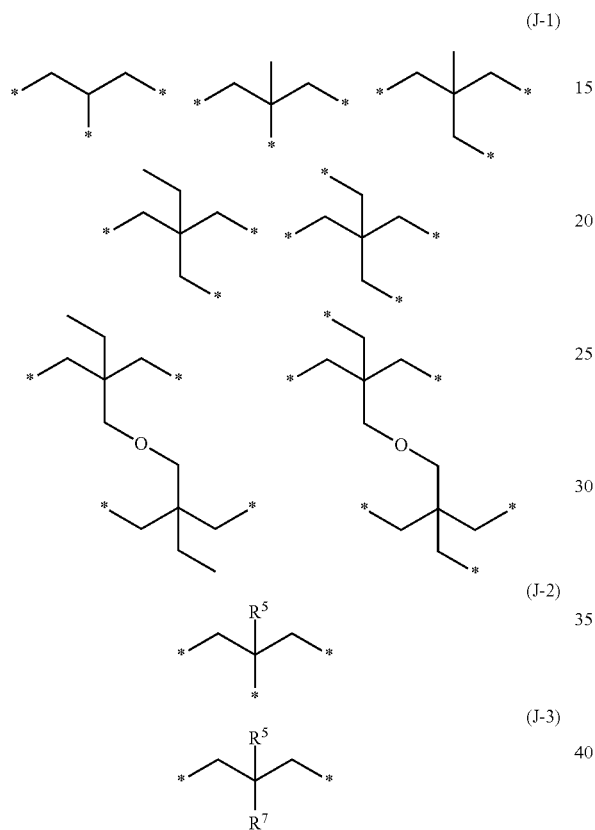

(J-1)

(J-2)

(J-3)

In the general formulae (J-2) and (J-3), each $R^5$ is a hydrogen atom or a methyl group, preferably a methyl group. $R^7$ is any of a (meth)acryloyloxy group, a styryloxy group, and an alkenyloxy group having 2 to 5 carbon atoms, preferably a (meth)acryloyloxy group. The alkenyloxy group having 2 to 5 carbon atoms may also be a vinyloxy group having 2 to 5 carbon atoms.

In the general formula (I), n is an integer of 1 to 5, and is, from the viewpoint of easy availability of raw materials, preferably 1 to 4, more preferably 1 or 2.

Specific examples of the unsaturated double bond-containing compound represented by the general formula (I) include the following compounds, and from the viewpoint of the oxygen absorption performance thereof, a unsaturated double bond-containing compound represented by the following general formula (II) is preferred.

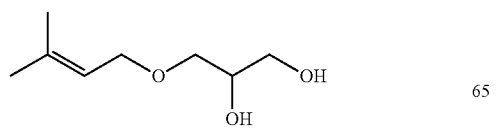

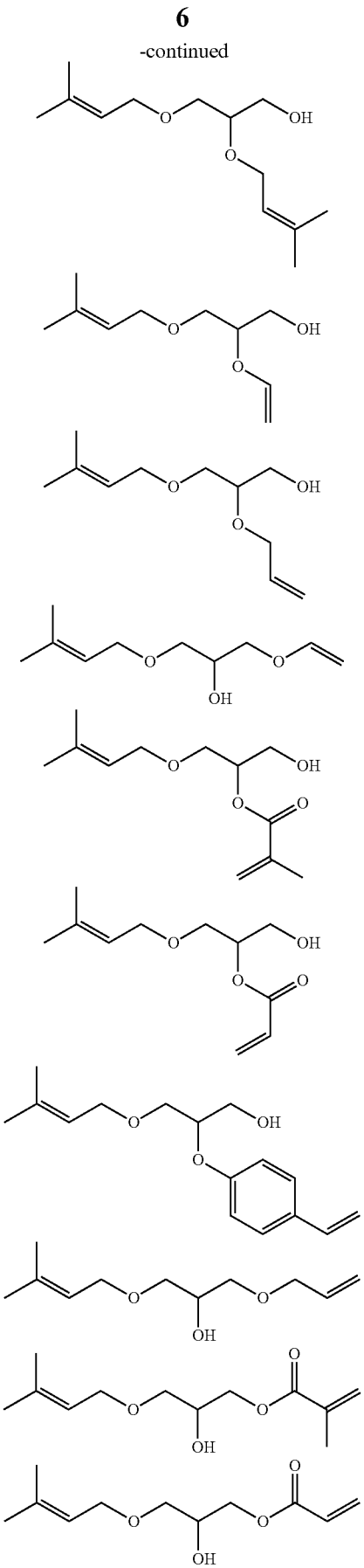

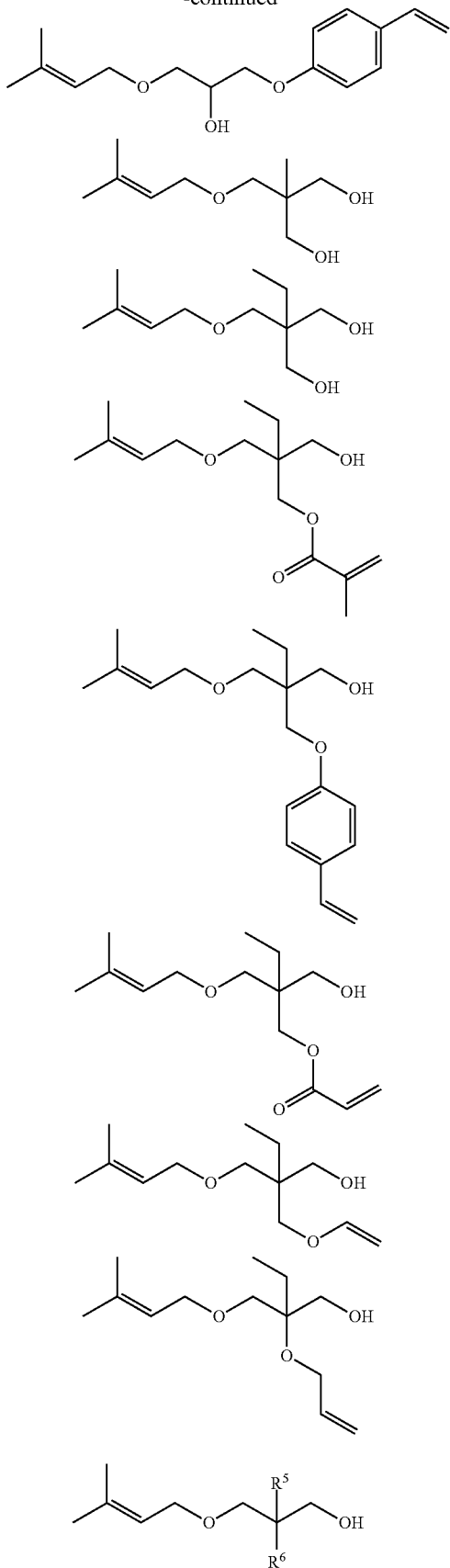

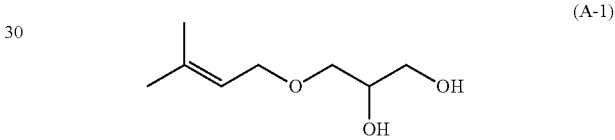

In the general formula (II), $R^5$ represents a hydrogen atom or a methyl group, $R^6$ represents any of a hydroxy group, a (meth)acryloyloxy group, a styryloxy group, and an alkenyloxy group having 2 to 5 carbon atoms.

In the general formula (II), $R^5$ represents a hydrogen atom or a methyl group, and is preferably a hydrogen atom. $R^6$ represents any of a hydroxy group, a (meth)acryloyloxy group, a styryloxy group, and an alkenyloxy group having 2 to 5 carbon atoms, and is preferably a hydroxy group or a (meth)acryloyloxy group. The alkenyloxy group having 2 to 5 carbon atoms may also be a vinyloxy group having 2 to 5 carbon atoms.

A production method for the unsaturated double bond-containing compound of the present invention is not specifically limited, and the compound can be produced according to known methods either singly or as combined. For example, in the case of producing an unsaturated double bond-containing compound represented by the following formula (A-1), a corresponding epoxy compound of 1-(3-methyl-2-butenoxy)-2,3-epoxy propane is reacted with water to be ring-opened in the presence of an acid catalyst such as sulfuric acid to give the intended compound. Regarding the reaction condition, from the viewpoint of achieving sufficient reaction, the reaction system is stirred at a temperature of approximately 25 to 70° C. for approximately 30 minutes to 10 hours.

(A-1)

[Oxygen Absorbent]

The oxygen absorbent of the present invention contains an unsaturated double bond-containing compound represented by the above-mentioned general formula (I). As described above, the unsaturated double bond-containing compound of the present invention has an excellent oxygen absorption performance and therefore, when the oxygen absorbent containing the compound is used in coating materials, this can sufficiently promote crosslinking reaction and curing reaction.

<Transition Metal Salt>

Containing the unsaturated double bond-containing compound of the present invention, the oxygen absorbent of the present invention has a sufficient oxygen absorption performance, and may further contain a transition metal salt for further improving the oxygen absorption performance thereof.

Examples of the transition metal to constitute the transition metal salt include transition metal elements of Period 4 such as titanium, vanadium, chromium, manganese, iron, cobalt, nickel and copper, and transition metal elements of Period 5 such as ruthenium and rhodium. Among these, from the viewpoint of improving the oxygen absorption performance of the oxygen absorbent, transition metal elements of Period 4 are preferred, manganese, iron, cobalt, nickel and copper are more preferred, and cobalt is even more preferred.

The counter ion to the transition metal in the transition metal salt is, from the viewpoint of compatibility, preferably an organic acid-derived anion species, and the organic acid is preferably an organic acid having 2 to 30 carbon atoms, which may be saturated or unsaturated, linear or branched, may have a cyclic structure or a substituent. Examples of the organic acid include acetic acid, stearic acid, dimethyldithiocarbamic acid, palmitic acid, 2-ethylhexanoic acid, neodecanoic acid, linolic acid, oleic acid, capric acid and naphthenic acid.

The transition metal salt for use in the present invention includes those produced by combining the transition metal and the counter ion in any desired manner, and is, from the viewpoint of the balance between the production cost and the oxygen absorption performance, preferably cobalt 2-ethylhexanoate, cobalt neodecanoate or cobalt stearate.

In the case where the oxygen absorbent contains a transition metal salt, the content of the salt is preferably 0.001 to 10 mol % relative to the vinyl group in the unsaturated double bond-containing compound, more preferably 0.005 to 5 mol %, even more preferably 0.01 to 1 mol %, further more preferably 0.1 to 1 mol %. When the content of the transition metal salt falls within the above range, the oxygen absorbent can be given a sufficient oxygen absorption performance.

<Content of Unsaturated Double Bond-Containing Compound in Oxygen Absorbent>

The content of the unsaturated double bond-containing compound represented by the general formula (I) in the oxygen absorbent of the present invention is, though not specifically limited but from the viewpoint of securing effective oxygen absorption, preferably 50% by mass or more, more preferably 60% by mass or more, even more preferably 70% by mass or more, further more preferably 80% by mass or more, still further more preferably 85% by mass or more, still further more preferably 90% by mass or more. From the viewpoint of the production cost of the oxygen absorbent, preferably, the content is substantially 100% by mass, more preferably 99.9% by mass or less, even more preferably 99.8% by mass or less.

<Optional Components in Oxygen Absorbent>

The oxygen absorbent of the present invention may contain various additives within a range not detracting from the advantageous effects of the present invention, in addition to the unsaturated double bond-containing compound represented by the general formula (I) an the transition metal salt. Specifically, the oxygen absorbent may contain a filler, a UV absorbent, a pigment, a tackifier, a contraction reducer, an antiaging agent, a plasticizer, an aggregate, a flame retardant, a stabilizer, a fiber reinforcing material, a dye, an antioxidant, a leveling agent, and an anti-sagging agent.

<Oxygen Absorption Amount>

The oxygen absorbent of the present invention exhibits an excellent oxygen absorption performance even at room temperature. Specifically, the oxygen absorption amount at 20° C. of the oxygen absorbent of the present invention containing a transition metal salt is, as a value after 1 day, preferably 4 mL/g or more, more preferably 5 mL/g or more, even more preferably 6 mL/g or more.

The oxygen absorption amount at 60° C. of the oxygen absorbent of the present invention containing a transition metal salt is, as a value after 1 day, preferably 15 mL/g or more, more preferably 20 mL/g or more, even more preferably 25 mL/g or more.

On the other hand, the oxygen absorption amount at 20° C. of the oxygen absorbent of the present invention not containing a transition metal salt is, as a value after 5 days, preferably 0.2 mL/g or more, more preferably 0.4 mL/g or more, even more preferably 0.6 mL/g or more.

The oxygen absorption amount at 60° C. of the oxygen absorbent of the present invention not containing a transition metal salt is, as a value after 5 days, preferably 10 mL/g or more, more preferably 20 mL/g or more, even more preferably 25 mL/g or more.

The upper limit of the oxygen absorption amount of the oxygen absorbent is not limited, and the oxygen absorption amount can be measured according to the method described in the section of Examples.

<Production Method for Oxygen Absorbent>

The oxygen absorbent of the present invention can be produced by mixing the unsaturated double bond-containing compound represented by the general formula (I) and optionally a transition metal salt and various additives. Specifically, the oxygen absorbent can be produced by stirring and mixing the unsaturated double bond-containing compound represented by the general formula (I) and a transition metal salt.

[Resin Composition]

The resin composition of the present invention contains the oxygen absorbent of the present invention and a resin. The unsaturated double bond-containing compound represented by the general formula (I) has a polymerizable group and a reactive group by itself, and therefore even when blended with a resin, the compound hardly interferes with crosslinking reaction or polymerization reaction of the resin. Consequently, the resin composition of the present invention is excellent in that it hardly lowers the yield of crosslinking reaction and polymerization reaction of the resin even in the presence of oxygen.

<Resin>

Not specifically limited, the resin for use in the resin composition of the present invention may be any resin usable in paints, adhesives, coating agents, etc. The resin may be a radical-polymerizable resin, or an active energy ray-curable resin such as a UV-curable resin. Though depending on the intended use, the resin is preferably an active energy-curable resin as remarkably achieving the advantageous effects of the present invention.

Specific examples of the resin include a resin curable through radical polymerization reaction, such as an unsaturated polyester resin, a vinyl ester resin, a polymerizable group-having (meth)acrylic resin, and a urethane (meth)acrylate resin;

and a resin requiring an oxygen barrier performance, such as a polyvinyl alcohol, an ethylene-vinyl acetate copolymer, a partially or completely saponified product of an ethylene-vinyl acetate copolymer, an epoxy resin, a polyester resin, a polyolefin resin, and a cyclic polyolefin resin.

Apart from these resins, a fluororesin, a polyamide resin such as polyamide 66, a polycarbonate resin and a polyurethane resin can also be used, as needed.

Examples of the unsaturated polyester resin include a copolymer of a polyalcohol compound and an α,ß-unsaturated polybasic acid compound and any other polybasic acid compound, such as a propylene glycol-phthalic anhydride-maleic anhydride copolymer, an ethylene glycol-phthalic anhydride-maleic anhydride, as well as those prepared by adding a radical-polymerizable monomer such as styrene to the copolymers.

Examples of the polyalcohol compound include ethylene glycol, 1,2-propanediol, 1,3-propanediol, neopentyl glycol, hydrogenated bisphenol A and hydrogenated bisphenol F.

Examples of the α,ß-unsaturated polybasic acid compound include maleic anhydride, maleic acid, fumaric acid, itaconic acid and citraconic acid. Examples of the polybasic acid compound include phthalic anhydride, phthalic acid, isophthalic acid, terephthalic acid, tetrahydrophthalic anhydride, HET acid, adipic acid and sebacic acid. One alone or two or more kinds of these may be used either singly or as combined.

These copolymers may further contain a glycidyl compound of an unsaturated alcohol such as allyl glycidyl ether, as one copolymerization component.

Examples of the vinyl ester resin include those produced by adding (meth)acrylic acid to an epoxy resin, such as those produced by adding (meth)acrylic acid to the terminal of a bisphenol A-type epoxy resin.

Examples of the urethane (meth)acrylate resin include those produced by adding (meth)acrylic acid to a remaining isocyanate group-containing polymer to be produced from a polyalcohol compound and an excessive polyisocyanate compound. The polyalcohol compound may be the same as the polyalcohol compound described hereinabove for the unsaturated polyester resin, and examples of the polyisocyanate compound include tolylene diisocyanate, diphenylmethane diisocyanate, isophorone diisocyanate, and hexamethylene diisocyanate.

<Content of Unsaturated Double Bond-Containing Compound in Resin Composition>

The content of the unsaturated double bond-containing compound represented by the general formula (I) in the resin composition of the present invention is preferably 0.1 to 50 parts by mass relative to 100 parts by mass of the resin, more preferably 0.2 to 30 parts by mass, even more preferably 0.5 to 10 parts by mass.

<Optional Component in Resin Composition>

The resin composition of the present invention may optionally contain a pigment, a dye, a filler, a UV absorbent, a tackifier, a contraction reducer, an antiaging agent, a plasticizer, an aggregate, a flame retardant, a stabilizer, a fiber reinforcing agent, an antioxidant, a leveling agent and an anti-sagging agent. Also the resin composition of the present invention may contain, as a diluent, for example, styrene and a (meth)acrylate, and from the viewpoint of polymerizability, a (meth)acrylate is especially preferred as more effectively exhibiting the advantageous effects of the present invention.

Examples of the pigment include titanium oxide, red iron oxide, aniline black, carbon black, cyanine blue, and chrome yellow. Examples of the filler include talc, mica, kaolin, calcium carbonate and clay.

<Production Method for Resin Composition>

The resin composition of the present invention can be produced by mixing a resin and the oxygen absorbent of the present invention. Specifically, the resin composition can be produced by mixing, for example, by stirring the oxygen absorbent of the present invention, a resin and any other optional components, as needed.

<Use of Resin Composition>

The resin composition of the present invention can be favorably used, for example, for paints, adhesives and coating agents.

EXAMPLES

Hereinunder, the present invention is described in detail with reference to Examples, but the present invention is not restricted to these Examples. In Examples and Comparative Examples, the physical data were measured according to the methods mentioned below.

[Oxygen Absorption Amount (20° C.)]

100 mg of the oxygen absorbent produced in Examples or Comparative Examples was accurately weighed, and put into a sample bottle having an internal volume of 20 mL. Subsequently, for moisture control inside the sample bottle, a small bottle containing 0.5 mL of ion-exchanged water was put into the sample bottle, and the opening mouth of the sample bottle was sealed up with a polytetrafluoroethylene resin-sealed rubber cap and an aluminum sealant. The sample bottle was put in a constant-temperature tank at 20° C., and after 1 day, 5 days and 15 days, the residual oxygen amount in the sample bottle was measured using a residual oxygen meter (Pack Master RO-103, from Iijima Electronics Industry Co., Ltd.). A reference sample bottle was prepared in the same manner as above except that the oxygen absorbent was not put thereinto, and left under the same condition, and the residual oxygen amount therein was measured in the same manner. A difference in the residual oxygen amount between the two was referred to as an oxygen absorption amount of the oxygen absorbent (20° C.) [mL/g]. The same test was repeated three times, and the data were averaged to give an average value.

[Oxygen Absorption Amount (60° C.)]

An oxygen absorption amount (60° C.) [mL/g] of the oxygen absorbent was measured in the same manner as above, except that, in the measurement of the oxygen absorption amount (20° C.), the temperature of the constant-temperature tank was changed from 20° C. to 60° C. (average value in 3 tests).

Example 1

Synthesis of 1-(3-methyl-2-butenoxy)-2,3-hydroxypropane

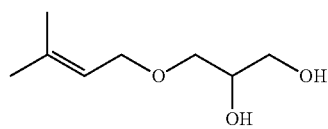

(A-1)

50.6 g of an aqueous 1 M sulfuric acid solution was put into a reactor equipped with a stirrer, a thermometer and a dropping funnel, in a nitrogen stream atmosphere. The internal temperature was kept at 20° C. or lower, 30.1 g (0.212 mol) of 1-(3-methyl-2-butenoxy)-2,3-epoxypropane was dropwise added thereto with stirring, and after the dropwise addition, this was heated up to 40° C. At an internal temperature of 40° C., this was stirred for 1 hour. The reaction liquid was neutralized with an aqueous 10 wt % sodium hydroxide solution, and extracted with toluene. The resultant organic layer was washed with saturated saline water, and the solvent was evaporated away under reduced pressure to give 8.0 g (0.048 mol; yield 23%) of 1-(3-methyl-2-butenoxy)-2,3-hydroxypropane of the above formula (A-1). Measurement results of its 1H-NMR are shown below.

$^1$H-NMR (400 MHz, CDCl$_3$, TMS) δ: 5.33 (thep, J=6.8, 1.6 Hz, 1H), 4.00 (d, J=6.8 Hz, 2H), 3.86 (dhex, J=3.6, 1.6 Hz, 1H), 3.68 (dd, J=11.6, 3.6 Hz, 1H), 3.58 (dd, J=11.6, 6.8 Hz, 1H), 3.50 (dd, J=9.0, 4.4 Hz, 1H), 3.45 (dd, J=9.0, 6.0 Hz, 1H), 3.36-3.30 (brs, 2H), 1.75 (s, 3H), 1.67 (s, 3H)

Example 2

In a glass-made sample bottle, 5.00 g (31.2 mmol) of 1-(3-methyl-2-butenoxy)-2,3-hydroxypropane and 23 mg (0.034 mmol; 0.11 mol % relative to the vinyl group in 1-(3-methyl-2-butenoxy)-2,3-hydroxypropane) of cobalt(II) stearate (from Wako Pure Chemical Industries Ltd.; purity 90%) were put and well stirred to give an oxygen absorbent. The evaluation results are shown in Table 1.

Example 3

An oxygen absorbent was produced in the same manner as in Example 2, except that cobalt(II) stearate was not added. The evaluation results are shown in Table 1.

Comparative Example 1

An oxygen absorbent was produced according to the same method as in Example 2, except that 1-(3-methyl-2-butenoxy)-2,3-hydroxypropane in Example 2 was changed to 5.00 g of a compound (E-1) of the following formula (from Tokyo Chemical Industry Co., Ltd.; purity 99%; 37.8 mmol) and the amount of cobalt(II) stearate was changed from 23 mg to 29 mg (0.046 mmol; 0.12 mol % relative to the vinyl group of the compound (E-1)). The evaluation results are shown in Table 1.

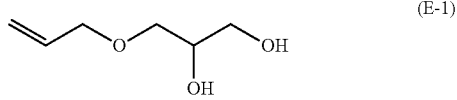

(E-1)

Comparative Example 2

An oxygen absorbent was produced according to the same method as in Example 3, except that 1-(3-methyl-2-butenoxy)-2,3-hydroxypropane in Example 3 was changed to 5.00 g of the compound (E-1) of the above formula (from Tokyo Chemical Industry Co., Ltd.; purity 99%). The evaluation results are shown in Table 1.

TABLE 1

| | | | after 1 day | after 5 days | after 15 days |
|---|---|---|---|---|---|
| Oxygen Absorption Amount (20° C.) [mL/g] | Example | 2 | 6.4 | 15.7 | 31.3 |
| | | 3 | 0.6 | 0.8 | 1.2 |
| | Comparative Example | 1 | 2.8 | 2.5 | 4.0 |
| | | 2 | 0.6 | 0.0 | 0.9 |
| Oxygen Absorption Amount (60° C.) [mL/g] | Example | 2 | 27.0 | 49.8 | 49.2 |
| | | 3 | 0.5 | 27.2 | 48.4 |
| | Comparative Example | 1 | 10.5 | 9.2 | 13.2 |
| | | 2 | 1.4 | 0.6 | 1.6 |

As shown in Table 1, it is known that the unsaturated double bond-containing compound of the present invention has an excellent oxygen absorption performance even at room temperature. Surprisingly, in addition, the compound can absorb oxygen even though a transition metal salt is not used, and can sufficiently achieve crosslinking reaction and curing reaction of a resin composition.

INDUSTRIAL APPLICABILITY

The oxygen absorbent of the present invention can be favorably used as an oxygen absorbent of inhibiting negative influences of oxygen on crosslinking reaction or curing reaction of a resin that requires a curing step accompanied by radical polymerization, such as an unsaturated polyester resin, a vinyl ester resin, a (meth)acrylic resin and a urethane (meth)acrylate resin. In addition, when mixed in a resin or applied to a surface, the oxygen absorbent can improve the oxygen barrier performance of a resin that requires an oxygen barrier performance, such as a polyvinyl alcohol, or a partially or completely saponified ethylene-vinyl acetate copolymer.

The invention claimed is:

1. An unsaturated double bond-containing compound represented by the following formula (II):

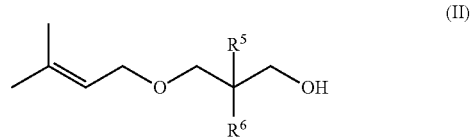

(II)

wherein $R^5$ represents a hydrogen atom or a methyl group, and $R^6$ represents any of a hydroxy group, a (meth)acryloyloxy group, a styryloxy group, and an alkenyloxy group having 2 to 5 carbon atoms.

2. The unsaturated double bond-containing compound according to claim 1, wherein $R^5$ in the general formula (II) is a hydrogen atom.

3. The unsaturated double bond-containing compound according to claim 1, wherein $R^6$ in the general formula (II) is a hydroxy group.

4. An oxygen absorbent comprising the unsaturated double bond-containing compound of claim 1.

5. The oxygen absorbent according to claim 4, containing a transition metal salt in an amount of 0.001 to 10 mol % relative to the vinyl group in the unsaturated double bond-containing compound.

6. A resin composition comprising the oxygen absorbent of claim 4, and a resin.

7. The resin composition according to claim 6, wherein the resin is an active energy ray-curable resin.

* * * * *